United States Patent
Rossi et al.

(10) Patent No.: US 11,225,665 B2
(45) Date of Patent: Jan. 18, 2022

(54) P38 MAP KINASE INHIBITORS

(71) Applicant: City of Hope, Duarte, CA (US)

(72) Inventors: John J. Rossi, Monrovia, CA (US); Sorah Yoon, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/902,029

(22) Filed: Jun. 15, 2020

(65) Prior Publication Data

US 2020/0399643 A1  Dec. 24, 2020

Related U.S. Application Data

(60) Provisional application No. 62/864,005, filed on Jun. 20, 2019.

(51) Int. Cl.
*C12N 15/113* (2010.01)

(52) U.S. Cl.
CPC .............. *C12N 15/1137* (2013.01)

(58) Field of Classification Search
CPC .................................. C12N 15/1137
See application file for complete search history.

(56) References Cited

U.S. PATENT DOCUMENTS

| | | |
|---|---|---|
| 9,388,418 B2 | 7/2016 | Rossi et al. |
| 9,464,293 B2 | 10/2016 | Rossi et al. |
| 9,506,064 B2 | 11/2016 | Rossi et al. |
| 9,953,131 B2 | 4/2018 | Rossi et al. |
| 10,041,071 B2 | 8/2018 | Rossi et al. |
| 10,272,165 B2 | 4/2019 | Rossi et al. |
| 10,369,167 B2 | 8/2019 | Pang et al. |
| 10,550,394 B2 | 2/2020 | Rossi et al. |
| 2015/0368645 A1 | 12/2015 | Rossi et al. |
| 2017/0043040 A1 | 2/2017 | Rossi et al. |
| 2017/0073684 A1 | 3/2017 | Rossi et al. |
| 2017/0226515 A1 | 8/2017 | Rossi et al. |
| 2017/0233740 A1 | 8/2017 | Rossi et al. |
| 2018/0125878 A1 | 5/2018 | Pang et al. |
| 2019/0343867 A1 | 11/2019 | Rossi et al. |
| 2020/0299696 A1 | 9/2020 | Rossi et al. |
| 2020/0354721 A1 | 11/2020 | Rossi et al. |

OTHER PUBLICATIONS

Hori, S-I. et al. (Jan. 3, 2018). "Current Advances in Aptamers for Cancer Diagnosis and Therapy," *Cancers* 10(1)9.

Yoon, S. et al. (Apr. 2017, e-published Feb. 15, 2017). "Future strategies for the discovery of therapeutic aptamers," *Expert Opin Drug Discov* 12(4):317-319.

Yoon, S. et al. (Jul. 2017, e-published Apr. 10, 2017). Blind SELEX Approach Identifies RNA Aptamers That Regulate EMT and Inhibit Metastasis, *Mol Cancer Res* 15(7):811-820.

Yoon, S. et al. (Mar. 1, 2019, e-published Dec. 1, 2018). "An RNA Aptamer Targeting the Receptor Tyrosine Kinase PDGFRα Induces Anti-tumor Effects through STAT3 and p53 in Glioblastoma," *Mol Ther Nucleic Acids* 14:131-141.

Yoon, S. et al. (Dec. 6, 2019, e-published Aug. 22, 2019). "Targeted Delivery of C/EBPα-saRNA by RNA Aptamers Shows Anti-tumor Effects in a Mouse Model of Advanced PDAC," *Mol Ther Nucleic Acids* 18:142-154.

Zhou, J. et al. (May 2009, e-published Mar. 21, 2009). "Selection, characterization and application of new RNA HIV gp 120 aptamers for facile delivery of Dicer substrate siRNAs into HIV infected cells," *Nucleic Acids Res* 37(9):3094-3109.

Zhou, J. et al. (Feb. 1, 2010). "Aptamer-targeted cell-specific RNA interference," *Silence* 1(1):4.

Zhou, J. et al. (Nov. 2, 2012). "Current progress of RNA aptamer-based therapeutics," *Front Genet* 3:234.

*Primary Examiner* — J. E. Angell

(74) *Attorney, Agent, or Firm* — Mintz, Levin, Cohn, Ferris, Glovsky and Popeo, P.C.

(57) ABSTRACT

Provided herein, inter alia, are p38 mitogen-activated protein kinase inhibitors and methods of treating cancer using p38 mitogen-activated protein kinase inhibitors.

20 Claims, 3 Drawing Sheets

Specification includes a Sequence Listing.

P38 MAP KINASE INHIBITORS

CROSS-REFERENCE TO RELATED APPLICATIONS

This application claims priority to U.S. Application No. 62/864,052 filed Jun. 20, 2019, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant no. NIHAII29329 awarded by the National Institute of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-724001US_SL_ST25.txt, created Jun. 12, 2020, 15,833 bytes, machine format IBM-PC, MS Windows operating system, is hereby incorporated by reference.

BACKGROUND

Mitogen-activated protein kinases are involved in various cellular responses to extracellular signals. Members of this family are Ser/Thr kinases that activate their substrates by phosphorylation. Mitogen-activated protein kinases are activated by a variety of signals including growth factors, cytokines, UV radiation, and stress-inducing agents. One particularly interesting mitogen-activated protein kinases is p38. p38, also known as cytokine suppressive anti-inflammatory drug binding protein and RK, has been isolated from murine pre-B cells that were transfected with the lipopolysaccharide receptor, CD14, and induced with LPS. p38 has since been isolated and sequenced, as has the cDNA encoding it in humans and mouse. Activation of p38 has been observed in cells stimulated by stress, such as treatment of lipopolysaccharides, UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis. Based upon this finding, it is believed that p38, along with other mitogen-activated protein kinases, have a role in mediating cellular response to inflammatory stimuli, such as leukocyte accumulation, macrophage/monocyte activation, tissue resorption, fever, acute phase responses and neutrophilia. In addition, mitogen-activated protein kinases, such as p38, have been implicated in cancer, thrombin-induced platelet aggregation, immunodeficiency disorders, autoimmune diseases, cell death, allergies, osteoporosis and neurodegenerative disorders. Inhibitors of p38 have also been implicated in the area of pain management through inhibition of prostaglandin endoperoxide synthase-2 induction. Drugs that specifically inhibit p38 mitogen-activated protein kinases are being developed. However, the efficacy of these p38 MAP kinase inhibitors is still being investigated. Accordingly, there is a need in the art to develop potent inhibitors of p38 MAP kinase that are useful in treating various conditions associated with p38 activation. Described herein, inter alia, are solutions to these and other problems in the art.

BRIEF SUMMARY

The disclosure provides oligonucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and homologs of each of the foregoing. In aspects, the oligonucleotides are ribonucleic acids. In aspects, the oligonucleotides are miRNA, mRNA, siRNA, or saRNA. In aspects, the oligonucleotides are aptamers that inhibit a p38γ mitogen-activated protein kinase. In aspects, the oligonucleotides are aptamers that inhibit phosphorylation of the p38γ mitogen-activated protein kinase.

The disclosure provides methods of inhibiting phosphorylation of p38γ mitogen-activated protein kinase by contacting p38γ mitogen-activated protein kinase with an effective amount of the oligonucleotide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a homolog of any one of the foregoing. In aspects, the oligonucleotides are ribonucleic acids. In aspects, the oligonucleotides are miRNA, mRNA, siRNA, or saRNA.

The disclosure provides method of treating cancer in a patient in need thereof by administering to the patient a effective amount the oligonucleotide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a homolog of any one of the foregoing. In aspects, the oligonucleotides are ribonucleic acids. In aspects, the oligonucleotides are miRNA, mRNA, siRNA, or saRNA. In aspects, the oligonucleotides are aptamers that inhibit a p38γ mitogen-activated protein kinase. In aspects, the oligonucleotides are aptamers that inhibit phosphorylation of the p38γ mitogen-activated protein kinase. In aspects, the cancer is breast cancer (e.g., triple negative breast cancer), prostate cancer, colon cancer, ovarian cancer, lymphoma (e.g., cutaneous T-cell lymphoma), bladder cancer, thyroid cancer, lung cancer, or head and neck squamous cell carcinoma.

The disclosure provides methods of suppressing proliferation of a cutaneous T-cell lymphoma cell by contacting the cutaneous T-cell lymphoma cell with an effective amount of the oligonucleotide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a homolog of any one of the foregoing. In aspects, the oligonucleotides are ribonucleic acids. In aspects, the oligonucleotides are miRNA, mRNA, siRNA, or saRNA.

The disclosure comprises complexes comprising: (i) a p38γ MAP kinase, and (ii) an oligonucleotide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a homolog of any one of the foregoing. In aspects, the oligonucleotides are ribonucleic acids. In aspects, the oligonucleotides are miRNA, mRNA, siRNA, or saRNA.

These and other embodiments and aspects of the disclosure are described herein.

BRIEF DESCRIPTION OF THE DRAWINGS

FIG. 1C shows the selection strategy used to obtain the oligonucleotides of SEQ ID NO:1 and SEQ ID NO:3 described herein.

DETAILED DESCRIPTION

Definitions

Figure 1A:
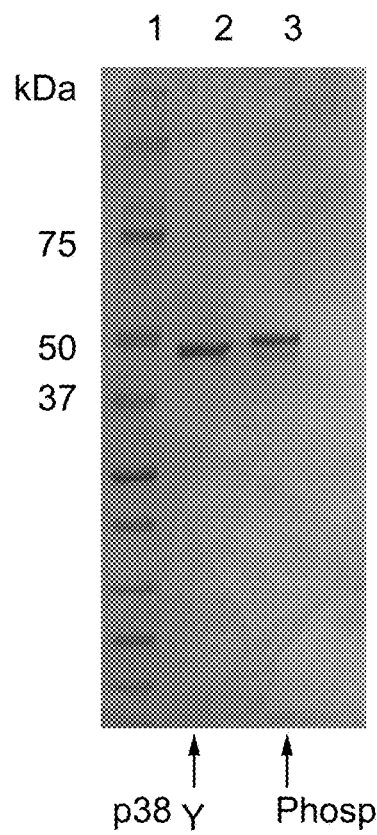
FIGS. 1A-1C show the process for obtaining the oligonucleotides described herein. The target proteins used in SELEX are phosphorylated p38γ comprising Tyr-182 and Thr-185 as shown by SDS-Page (FIG. 1A) and Western Blot (FIG. 1B).

The terms "p38 kinase," "p38 mitogen-activated protein kinase," "p38 MAP kinase," and/or "p38" are here used interchangeably and according to their common, ordinary meaning and refer to proteins of the same or similar names and functional fragments and homologs thereof. The term includes recombinant or naturally occurring forms of, or variants thereof, that maintain p38 kinase activity (e.g. within at least 30%, 40%, 50%, 60%, 70%, 80%, 90%, 95%, or 100% activity compared to p38 kinase). The p38 kinases have four isoforms including p38α (MAPK14, SEQ ID NO:11), p38β (MAPK11, SEQ ID NO:12), p38γ (MAPK12, SEQ ID NO:13), and p38δ (MAPK13, SEQ ID NO:14). The role of p38 MAP kinases in cancer is described, for example, by Koul et al, Genes Cancer, 4(9-10):342-359 (2013).

The terms "p38alpha (p38α)" or "mitogen-activated protein kinase 14 (MAPK14)" (e.g. Protein Data Bank ID: 5ML5 or 5MQV; SEQ ID NO:11) are here used interchangeably and according to their common, ordinary meaning and refer to proteins of the same or similar names and functional fragments and homologs thereof. The term includes any recombinant or naturally occurring form of, or variants thereof that maintain p38α activity (e.g. within at least 30%, 40%, 50%, 60%, 70%, 80%, 90%, 95%, or 100% activity compared to p38α).

The terms "p38beta (p38β)" or "mitogen-activated protein kinase 11 (MAPK11)" (e.g. Protein Data Bank ID: 3GC7, 3GC8 or 3GC9; SEQ ID NO:12) are here used interchangeably and according to their common, ordinary meaning and refer to proteins of the same or similar names and functional fragments and homologs thereof. The term includes any recombinant or naturally occurring form of, or variants thereof that maintain p38β activity (e.g. within at least 30%, 40%, 50%, 60%, 70%, 80%, 90%, 95%, or 100% activity compared to p38β).

The terms "p38gamma (p38γ)" or "mitogen-activated protein kinase 12 (MAPK12)" (e.g., Protein Data Bank ID: 4QUM or 4QUN; SEQ ID NO:13) are here used interchangeably and according to their common, ordinary meaning and refer to proteins of the same or similar names and functional fragments and homologs thereof. The term includes any recombinant or naturally occurring form of, or variants thereof that maintain p38γ activity (e.g., within at least 30%, 40%, 50%, 60%, 70%, 80%, 90%, 95%, or 100% activity compared to p38γ).

The terms "p38delta (p38δ)" or "mitogen-activated protein kinase 13 (MAPK13)" (e.g. Protein Data Bank ID: 4MYG, 5EKN or 5EKO; SEQ ID NO:14) are here used interchangeably and according to their common, ordinary meaning and refer to proteins of the same or similar names and functional fragments and homologs thereof. The term includes any recombinant or naturally occurring form of, or variants thereof that maintain p38δ activity (e.g., within at least 30%, 40%, 50%, 60%, 70%, 80%, 90%, 95%, or 100% activity compared to p386).

The terms "p38 inhibitors" or "p38 kinase inhibitors" or "p38 MAP kinase inhibitors" are agents (e.g. compounds) that reduce the activity, levels and/or expression of p38 relative to the absence of the inhibitor. In aspects, these p38 kinase inhibitors can sufficiently inhibit the activities of one or more p38 related protein kinases or proteins in p38 related signal transduction cascades. In aspects, the p38 kinase inhibitors sufficiently suppress or downregulate the expression of p38 kinases, for example, by affecting or suppressing transcription level of mRNA of p38 kinase, protein expression level thereof or other indications for related genes thereof. Non-limiting examples of the p38 inhibitors include small molecules (e.g. synthetic small molecules or natural products and derivatives thereof), antibodies (e.g. monoclonal antibodies), nucleic acids (e.g. siRNA, microRNA and anti-microRNA), and peptides. In aspects, the p38 inhibitor comprises SEQ ID NO:1 or a homolog thereof. In aspects, the p38 inhibitor comprises SEQ ID NO:2 or a homolog thereof. In aspects, the p38 inhibitor comprises SEQ ID NO:3 or a homolog thereof. In aspects, the p38 inhibitor comprises SEQ ID NO:4 or a homolog thereof. In aspects, the p38 inhibitor comprises SEQ ID NO:5 or a homolog thereof. In aspects, the p38 inhibitor comprises SEQ ID NO:6 or a homolog thereof. In aspects, the p38 inhibitor comprises SEQ ID NO:7 or a homolog thereof. In aspects, the p38 inhibitor comprises SEQ ID NO:8 or a homolog thereof.

The term "aptamer" as provided herein refers to oligonucleotides (e.g., short oligonucleotides or deoxyribonucleotides), that bind (e.g. with high affinity and specificity) to proteins, peptides, and small molecules. In aspects, the aptamer is a ribonucleic acid that binds to a p38 MAP kinase. In aspects, the aptamer is a ribonucleic acid that binds to a p38γ MAP kinase. In aspects, the aptamer is a ribonucleic acid that selectively and with high affinity binds to a p38γ MAP kinase over other isoforms of p38 MAP kinase, such as p38α, p38β, and p38δ. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990)); in vitro selection of RNA molecules that bind specific ligands (Tuerk et al, Nature 346:818-822 (1990)); systematic evolution of ligands by exponential enrichment: RNA ligands to bacteriophage T4 DNA polymerase (Science 249:505-510); or by developing SOMAmers (slow off-rate modified aptamers) (Gold (2010)). Aptamer-based multiplexed proteomic technology for biomarker discovery. (PLoS ONE 5(12):e15004). Applying the SELEX and the SOMAmer technology includes adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells using apatmers.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In aspects, inhibition means negatively affecting (e.g. decreasing) the concentration or levels of the protein relative to the concentration or level of the protein in the absence of the inhibitor. In aspects, inhibition refers to reduction of a disease or symptoms of disease. In aspects, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a reduction of activity of a target protein resulting from a direct interaction (e.g. an inhibitor binds to the target protein). In aspects, inhibition refers to a reduction of activity of a target protein from an indirect interaction (e.g. an inhibitor binds to a protein that activates the target protein, thereby preventing target protein activation).

In embodiments, the term "inhibition," "inhibit," "inhibiting" and the like means negatively affecting (e.g. decreasing or suppressing) the expression of the protein relative to the expression level of the protein in the absence of the inhibitor. In aspects, inhibition means negatively affecting (e.g. decreasing or suppressing) transcription or expression level of mRNA of the protein relative to the transcription or expression level of the mRNA of the protein in the absence of the inhibitor. In aspects, inhibition means negatively affecting (e.g. decreasing or suppressing) expression level of the protein relative to the expression level of the protein in the absence of the inhibitor by elevating or increasing a concentration of a biological molecule which negatively affecting (e.g. decreasing or suppressing) the expression level of the protein.

An amino acid residue in a protein "corresponds" to a given residue when it occupies the same essential structural position within the protein as the given residue.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives, or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T); (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Thus, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. In aspects, identity exists over a region that is at least about 10 amino acids or nucleotides in length, or over a region that is 10-50 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In aspects, the amino acid side chain may be a non-natural amino acid side chain. In aspects, the amino acid side chain is H,

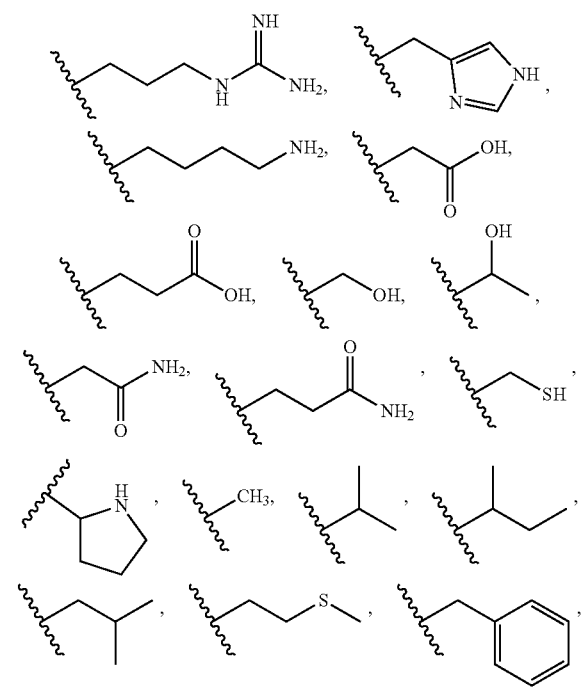

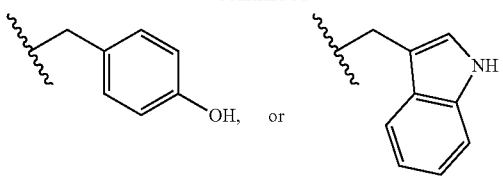

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-aminobicyclo[2.2.1]hept-5-ene-2-carboxylic acid hydrochloride, cis-2-aminocycloheptanecarboxylic acid hydrochloride, cis-6-amino-3-cyclohexene-1-carboxylic acid hydrochloride, cis-2-amino-2-methylcyclohexanecarboxylic acid hydrochloride, cis-2-amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl]-acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, and 4-(Hydroxymethyl)-D-phenylalanine.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In aspects, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, Scientific American, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In aspects, the antisense nucleic acid hybridizes to the target nucleic acid in vitro. In aspects, the antisense nucleic acid hybridizes to the target nucleic acid in a cell. In aspects, the antisense nucleic acid hybridizes to the target nucleic acid in an organism. In aspects, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, Anal. Biochem., 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In aspects, a siRNA or RNAi is a nucleic acid that has substantial or complete identity to a target gene and forms a double stranded siRNA. In aspects, the siRNA inhibits gene expression by interacting with a complementary cellular mRNA thereby interfering with the expression of the complementary mRNA. Typically, the nucleic acid is at least about 20-100 nucleotides in length (e.g., each complementary sequence of the double stranded siRNA is 20-100 nucleotides in length, and the double stranded siRNA is about 20-100 base pairs in length). In aspects, the length is 25-90 base nucleotides, about 30-90 or about 40-80 nucleotides in length.

A "saRNA," or "small activating RNA" as provided herein refers to a nucleic acid that forms a double stranded RNA, which double stranded RNA has the ability to increase or activate expression of a gene or target gene when expressed in the same cell as the gene or target gene. The complementary portions of the nucleic acid that hybridize to form the double stranded molecule typically have substantial or complete identity. In aspects, a saRNA is a nucleic acid that has substantial or complete identity to a target gene and forms a double stranded saRNA. Typically, the nucleic acid is at about 20-100 nucleotides in length (e.g., each complementary sequence of the double stranded saRNA is 20-100 nucleotides in length, and the double stranded saRNA is about 20-100 base pairs in length). In aspects, the length is 25-90 base nucleotides, about 30-90 or about 40-80 nucleotides in length.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 Molecular Cloning: A Laboratory Manual, 18.1-18.88.

The terms "Histone deacetylase (HDAC) inhibitors (HDACi or HDIs)" are used to indicate any molecules that sufficiently inhibit the activities (e.g. acetylation) of the histone deacetylases. In addition, these HDAC inhibitors inhibit activities (e.g. acetylation) of the proteins or enzymes included in nonhistone transcription factors and transcriptional co-regulators by increasing or repressing the transcription of genes such as ACTR, cMyb, E2F1, EKLF, FEN 1, GATA, HNF-4, HSP90, Ku70, NF-κB, PCNA, p53, RB, Runx, SF1 Sp3, STAT, TFIIE, TCF, YY1, and the like. Non-limiting examples of the HDAC inhibitors include HDAC5 inhibitor, HDAC6 inhibitor, HDAC10 inhibitor, and HDAC11 inhibitor. Non-limiting examples of the HDAC inhibitors include small molecules (e.g. synthetic small molecules or natural products and derivatives thereof), antibodies (e.g. monoclonal antibodies), nucleic acids (e.g. siRNA, microRNA and anti-microRNA), and peptides. Non-limiting examples of the small molecules as HDACi include HDAC inhibitors include vorinostat (SAHA), romidepsin, abexinostat, CI-994, belinostat, panobinostat, givinostat, entinostat, mocetinostat, trichostatin, SRT501, CUDC-101, JNJ-26481585, quisinostat, RGFP109 or PCI24781.

The term "pharmaceutically acceptable salts" is meant to include salts of the active compounds that are prepared with relatively nontoxic acids or bases, depending on the particular substituents found on the compounds described herein. When compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds contain both basic and acidic functionalities that allow the compounds to be converted into either base or acid addition salts.

"Pharmaceutically acceptable excipient" and "pharmaceutically acceptable carrier" refer to a substance that aids the administration of an active agent to and absorption by a subject and can be included in the compositions without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds. One of skill in the art will recognize that other pharmaceutical excipients are useful.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating is preventing. In aspects, treating does not include preventing.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In aspects, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect, and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In aspects, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may also include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be cystic fibrosis transmembrane conductance regulator. Thus, activation includes, at least in part, partially or totally increasing stimulation, increasing, promoting, or expediting activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions can be delivered transdermally, by a topical route, or formulated as applicator sticks, solutions, suspensions, emulsions, gels, creams, ointments, pastes, jellies, paints, powders, and aerosols. Co-administration includes administering one active agent (e.g. a complex described herein) within 0.5, 1, 2, 4, 6, 8, 10, 12, 16, 20, or 24 hours of a second active agent (e.g. anti-constipation or anti-dry eye agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In aspects, the active agents can be formulated separately. The active and/or adjunctive agents may be linked or conjugated to one another. The compounds described herein may be combined with treatments for constipation and dry eye disorders.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions n may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In aspects, the formulations of the compositions can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The compounds described herein can be used in combination with one another, with other active drugs known to be useful in treating a disease (e.g. cancer or CTCL) or with adjunctive agents that may not be effective alone, but may contribute to the efficacy of the active agent. Thus, the compounds described herein may be co-administered with one another or with other active drugs known to be useful in treating a disease.

As used herein, the term "cancer" refers to all types of cancer, neoplasm, or malignant tumors found in mammals, including leukemia, carcinomas and sarcomas. Exemplary cancers include acute myeloid leukemia, chronic myelogenous leukemia, and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas cancer, prostate cancer, breast cancer including triple negative breast cancer, and cutaneous T-cell lymphoma.

The term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "cutaneous T-cell lymphoma" or "CTCL" refers to a typical T-cell lymphoma that involves skin, although CTCL also can involve the blood, the lymph nodes, and other internal organs. Non-limiting examples of CTCL include mycosis fungoides and Sézary syndrome. For instance, mycosis fungoides is the most common type of CTCL constituting half cases of all CTCLs, which may cause various skin symptoms such as patches, plaques, or tumors. Sézary syndrome is an advanced, variant form of mycosis fungoides, which can be characterized by the presence of lymphoma cells (e.g., B-cells or T-cells) in the blood.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In aspects, anticancer agents herein may include epigenetic inhibitors and multi- or specific kinase inhibitors.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Non-limiting examples of HDAC inhibitors include vorinostat (SAHA), romidepsin, abexinostat, CI-994, belinostat, panobinostat, givinostat, entinostat, mocetinostat, trichostatin, SRT501, CUDC-101, JNJ-26481585, quisinostat, RGFP109 or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

"Selective" or "selectivity" or the like of a compound refers to the compound's ability to discriminate between molecular targets (e.g. a compound having selectivity toward one or more of p38 kinases (p38α, p38β, p38γ and p38δ) or MAPK (e.g. MAPK 11, MAPK12, MAPK 13 and MAPK14)). In aspects, the ribonucleic acids described herein have selectivity for p38γ kinase over p38α, p38β, and p38δ kinases.

"Specific", "specifically", "specificity", or the like of the ability of the ribonucleic acids described herein to cause a particular action, such as inhibition, to a particular molecular target with minimal or no action to other proteins in the cell (e.g., the ribonucleic acids described herein have specificity towards p38 gamma kinase (p38γ) or MAPK12 displays inhibition of the activity of those proteins including suppression of expression thereof as well as inhibition of enzyme properties). Meanwhile, the ribonucleic acids described herein display little-to-no inhibition of other p38 kinases such as p38α, p38β and p38δ or MAPK such as MAPK 11, MAPK 13 and MAPK14.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

In embodiments, the disclosure provides a ribonucleic acid comprising the sequence: GGGAGACAAGAAUAAACGCUCAAGUGUUUUUGAAGCGUCAGCUAUAGUUGGUCUUC UUAGAGCUUCGACAGGAGGCUCACAACAGGC (SEQ ID NO:1). In SEQ ID NO:1, each U and each C is a 2F'-modified pyrimidine. In aspects, the disclosure provides a ribonucleic acid having at least 50% sequence identity to SEQ ID NO:1. In aspects, the ribonucleic acid has at least 55% sequence identity to SEQ ID NO:1. In aspects, the ribonucleic acid has at least 60% sequence identity to SEQ ID NO:1. In aspects, the ribonucleic acid has at least 65% sequence identity to SEQ ID NO:1. In aspects, the ribonucleic acid has at least 70% sequence identity to SEQ ID NO:1. In aspects, the ribonucleic acid has at least 75% sequence identity to SEQ ID NO:1. In aspects, the ribonucleic acid has at least 80% sequence identity to SEQ ID NO:1. In aspects, the ribonucleic acid has at least 85% sequence identity to SEQ ID NO:1. In aspects, the ribonucleic acid has at least 88% sequence identity to SEQ ID NO:1. In aspects, the ribonucleic acid has at least 90% sequence identity to SEQ ID NO:1. In aspects, the ribonucleic acid has at least 92% sequence identity to SEQ ID NO:1. In aspects, the ribonucleic acid has at least 94% sequence identity to SEQ ID NO:1. In aspects, the ribonucleic acid has at least 95% sequence identity to SEQ ID NO:1. In aspects, the ribonucleic acid has at least 96% sequence identity to SEQ ID NO:1. In aspects, the ribonucleic acid has at least 98% sequence identity to SEQ ID NO:1. In aspects, the disclosure provides pharmaceutical compositions comprising any of the oligonucleotides described herein and a pharmaceutically acceptable excipient.

In aspects, the ribonucleic acid comprising SEQ ID NO:1 (and homologs thereof) is an miRNA. In aspects, the ribonucleic acid comprising SEQ ID NO:1 (and homologs thereof) is an mRNA. In aspects, the ribonucleic acid comprising SEQ ID NO:1 (and homologs thereof) is an siRNA. In aspects, the ribonucleic acid comprising SEQ ID NO:1 (and homologs thereof) is an saRNA. In aspects, the ribonucleic acid comprising SEQ ID NO:1 (and homologs thereof) is an aptamer. In aspects, the ribonucleic acid comprising SEQ ID NO:1 (and homologs thereof) is an aptamer that is capable of binding to a p38 mitogen-activated protein kinase. In aspects, the ribonucleic acid comprising SEQ ID NO:1 (and homologs thereof) is an aptamer that is capable of inhibiting the activity of a p38 mitogen-activated protein kinase. In aspects, the ribonucleic acid comprising SEQ ID NO:1 (and homologs thereof) is an aptamer that is capable of binding to and inhibiting the activity of a p38 mitogen-activated protein kinase. In aspects, the ribonucleic acid comprising SEQ ID NO:1 (and homologs thereof) is an aptamer that is capable of inhibiting phosphorylation of a p38 mitogen-activated protein kinase. In aspects, the ribonucleic acid comprising SEQ ID NO:1 (and homologs thereof) is an aptamer that is capable of binding to a p38 mitogen-activated protein kinase. In aspects, the ribonucleic acid comprising SEQ ID NO:1 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: GUGUUUUUGAAGCGUCAGCUAUAGUUGGUCUUCUUAGAGC (SEQ ID NO:2). In SEQ ID NO:2, each U and each C is a 2F'-modified pyrimidine. In aspects, the disclosure provides a ribonucleic acid having at least 50% sequence identity to SEQ ID NO:2. In aspects, the ribonucleic acid has at least 55% sequence identity to SEQ ID NO:2. In aspects, the ribonucleic acid has at least 60% sequence identity to SEQ ID NO:2. In aspects, the ribonucleic acid has at least 65% sequence identity to SEQ ID NO:2. In aspects, the ribonucleic acid has at least 70% sequence identity to SEQ ID NO:2. In aspects, the ribonucleic acid has at least 75% sequence identity to SEQ ID NO:2. In aspects, the ribonucleic acid has at least 80% sequence identity to SEQ ID NO:2. In aspects, the ribonucleic acid has at least 85% sequence identity to SEQ ID NO:2. In aspects, the ribonucleic acid has at least 90% sequence identity to SEQ ID NO:2. In aspects, the ribonucleic acid has at least 92% sequence identity to SEQ ID NO:2. In aspects, the ribonucleic acid has at least 94% sequence identity to SEQ ID NO:2. In aspects, the ribonucleic acid has at least 95% sequence identity to SEQ ID NO:2. In aspects, the ribonucleic acid has at least 96% sequence identity to SEQ ID NO:2. In aspects, the ribonucleic acid has at least 98% sequence identity to SEQ ID NO:2. In aspects, the disclosure provides pharmaceutical compositions comprising any of the oligonucleotides described herein and a pharmaceutically acceptable excipient. In aspects, the ribonucleic acid comprising SEQ ID NO:2 (and homologs thereof) is an miRNA, mRNA, siRNA, or saRNA. In aspects, the ribonucleic acid comprising SEQ ID NO:2 (and homologs thereof) is an aptamer that is capable of binding to a p38 mitogen-activated protein kinase. In aspects, the ribonucleic acid comprising SEQ ID NO:2 (and homologs thereof) is an aptamer that is capable of inhibiting the activity of a p38 mitogen-activated protein kinase. In aspects, the ribonucleic acid comprising SEQ ID NO:2 (and homologs thereof) is an aptamer that is capable of binding to and inhibiting the activity of a p38 mitogen-activated protein kinase. In aspects, the ribonucleic acid comprising SEQ ID NO:2 (and homologs thereof) is an aptamer that is capable of inhibiting phosphorylation of a p38 mitogen-activated protein kinase. In aspects, the ribonucleic acid comprising SEQ ID NO:2 (and homologs thereof) is an aptamer that is capable of binding to a p38 mitogen-activated protein kinase. In aspects, the ribonucleic acid comprising SEQ ID NO:2 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: GGGAGACAAGAAUAAACGCUCAAAACAGCGUUUGCUAUAGUUGGUCUCUCCUAAUC AACGAGCUUCGACAGGAGGCUCACAACAGGC (SEQ ID NO:3).

In SEQ ID NO:3, each U and each C is a 2F'-modified pyrimidine. In aspects, the disclosure provides a ribonucleic acid having at least 50% sequence identity to SEQ ID NO:3. In aspects, the ribonucleic acid has at least 55% sequence identity to SEQ ID NO:3. In aspects, the ribonucleic acid has at least 60% sequence identity to SEQ ID NO:3. In aspects, the ribonucleic acid has at least 65% sequence identity to SEQ ID NO:3. In aspects, the ribonucleic acid has at least 70% sequence identity to SEQ ID NO:3. In aspects, the ribonucleic acid has at least 75% sequence identity to SEQ ID NO:3. In aspects, the ribonucleic acid has at least 80% sequence identity to SEQ ID NO:3. In aspects, the ribonucleic acid has at least 85% sequence identity to SEQ ID NO:3. In aspects, the ribonucleic acid has at least 88% sequence identity to SEQ ID NO:3. In aspects, the ribonucleic acid has at least 90% sequence identity to SEQ ID NO:3. In aspects, the ribonucleic acid has at least 92% sequence identity to SEQ ID NO:3. In aspects, the ribonucleic acid has at least 94% sequence identity to SEQ ID NO:3. In aspects, the ribonucleic acid has at least 95% sequence identity to SEQ ID NO:3. In aspects, the ribonucleic acid has at least 96% sequence identity to SEQ ID NO:3. In aspects, the ribonucleic acid has at least 98% sequence identity to SEQ ID NO:3. In aspects, the disclosure provides pharmaceutical compositions comprising any of the ribonucleic acids described herein and a pharmaceutically acceptable excipient.

In aspects, the ribonucleic acid comprising SEQ ID NO:3 (and homologs thereof) is an miRNA. In aspects, the ribonucleic acid comprising SEQ ID NO:3 (and homologs thereof) is an mRNA. In aspects, the ribonucleic acid comprising SEQ ID NO:3 (and homologs thereof) is an siRNA. In aspects, the ribonucleic acid comprising SEQ ID NO:3 (and homologs thereof) is an saRNA. In aspects, the ribonucleic acid comprising SEQ ID NO:3 (and homologs thereof) is an aptamer. In aspects, the ribonucleic acid comprising SEQ ID NO:3 (and homologs thereof) is an aptamer that is capable of binding to a p38 mitogen-activated protein kinase. In aspects, the ribonucleic acid comprising SEQ ID NO:3 (and homologs thereof) is an aptamer that is capable of inhibiting the activity of a p38 mitogen-activated protein kinase. In aspects, the ribonucleic acid comprising SEQ ID NO:3 (and homologs thereof) is an aptamer that is capable of binding to and inhibiting the activity of a p38 mitogen-activated protein kinase. In aspects, the ribonucleic acid comprising SEQ ID NO:3 (and homologs thereof) is an aptamer that is capable of inhibiting phosphorylation of a p38 mitogen-activated protein kinase. In aspects, the ribonucleic acid comprising SEQ ID NO:3 (and homologs thereof) is an aptamer that is capable of binding to a p38 mitogen-activated protein kinase. In aspects, the ribonucleic acid comprising SEQ ID NO:3 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: AACAGCGUUUGC-UAUAGUUGGUCUCUCCUAAUCAACGAGC (SEQ ID NO:4). In SEQ ID NO:4, each U and each C is a 2F'-modified pyrimidine. In aspects, the disclosure provides a ribonucleic acid having at least 50% sequence identity to SEQ ID NO:4. In aspects, the ribonucleic acid has at least 55% sequence identity to SEQ ID NO:4. In aspects, the ribonucleic acid has at least 60% sequence identity to SEQ ID NO:4. In aspects, the ribonucleic acid has at least 65% sequence identity to SEQ ID NO:4. In aspects, the ribonucleic acid has at least 70% sequence identity to SEQ ID NO:4. In aspects, the ribonucleic acid has at least 75% sequence identity to SEQ ID NO:4. In aspects, the ribonucleic acid has at least 80% sequence identity to SEQ ID NO:4. In aspects, the ribonucleic acid has at least 85% sequence identity to SEQ ID NO:4. In aspects, the ribonucleic acid has at least 90% sequence identity to SEQ ID NO:4. In aspects, the ribonucleic acid has at least 92% sequence identity to SEQ ID NO:4. In aspects, the ribonucleic acid has at least 94% sequence identity to SEQ ID NO:4. In aspects, the ribonucleic acid has at least 95% sequence identity to SEQ ID NO:4. In aspects, the ribonucleic acid has at least 96% sequence identity to SEQ ID NO:4. In aspects, the ribonucleic acid has at least 98% sequence identity to SEQ ID NO:4. In aspects, the disclosure provides pharmaceutical compositions comprising any of the oligonucleotides described herein and a pharmaceutically acceptable excipient. In aspects, the ribonucleic acid comprising SEQ ID NO:4 (and homologs thereof) is an miRNA, mRNA, siRNA, or saRNA. In aspects, the ribonucleic acid comprising SEQ ID NO:4 (and homologs thereof) is an aptamer that is capable of binding to a p38 mitogen-activated protein kinase. In aspects, the ribonucleic acid comprising SEQ ID NO:4 (and homologs thereof) is an aptamer that is capable of inhibiting the activity of a p38 mitogen-activated protein kinase. In aspects, the ribonucleic acid comprising SEQ ID NO:4 (and homologs thereof) is an aptamer that is capable of binding to and inhibiting the activity of a p38 mitogen-activated protein kinase. In aspects, the ribonucleic acid comprising SEQ ID NO:4 (and homologs thereof) is an aptamer that is capable of inhibiting phosphorylation of a p38 mitogen-activated protein kinase. In aspects, the ribonucleic acid comprising SEQ ID NO:4 (and homologs thereof) is an aptamer that is capable of binding to a p38 mitogen-activated protein kinase. In aspects, the ribonucleic acid comprising SEQ ID NO:4 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: GGGA-GACAAGAATAAACGCTCAACAATCAGCGC-CATCGTTGGTTGGGGTGCTTGTTTC CTGCCTTCGACAGGAGGCTCACAACAGGC (SEQ ID NO:5). In SEQ ID NO:5, each U and each C is a 2F'-modified pyrimidine. In aspects, the disclosure provides a ribonucleic acid having at least 50% sequence identity to SEQ ID NO:5. In aspects, the ribonucleic acid has at least 55% sequence identity to SEQ ID NO:5. In aspects, the ribonucleic acid has at least 60% sequence identity to SEQ ID NO:5. In aspects, the ribonucleic acid has at least 65% sequence identity to SEQ ID NO:5. In aspects, the ribonucleic acid has at least 70% sequence identity to SEQ ID NO:5. In aspects, the ribonucleic acid has at least 75% sequence identity to SEQ ID NO:5. In aspects, the ribonucleic acid has at least 80% sequence identity to SEQ ID NO:5. In aspects, the ribonucleic acid has at least 85% sequence identity to SEQ ID NO:5. In aspects, the ribonucleic acid has at least 90% sequence identity to SEQ ID NO:5. In aspects, the ribonucleic acid has at least 92% sequence identity to SEQ ID NO:5. In aspects, the ribonucleic acid has at least 94% sequence identity to SEQ ID NO:5. In aspects, the ribonucleic acid has at least 95% sequence identity to SEQ ID NO:5. In aspects, the ribonucleic acid has at least 96% sequence identity to SEQ ID NO:5. In aspects, the ribonucleic acid has at least 98% sequence identity to SEQ ID NO:5. In aspects, the disclosure provides pharmaceutical compositions comprising any of the ribonucleic acids described herein and a pharmaceutically acceptable excipient.

In aspects, the ribonucleic acid comprising SEQ ID NO:5 (and homologs thereof) is an miRNA. In aspects, the ribonucleic acid comprising SEQ ID NO:5 (and homologs thereof) is an mRNA. In aspects, the ribonucleic acid comprising SEQ ID NO:5 (and homologs thereof) is an siRNA. In aspects, the ribonucleic acid comprising SEQ ID NO:5 (and homologs thereof) is an saRNA. In aspects, the ribonucleic acid comprising SEQ ID NO:5 (and homologs thereof) is an aptamer. In aspects, the ribonucleic acid comprising SEQ ID NO:5 (and homologs thereof) is an aptamer that is capable of binding to a p38 mitogen-activated protein kinase. In aspects, the ribonucleic acid comprising SEQ ID NO:5 (and homologs thereof) is an aptamer that is capable of inhibiting the activity of a p38 mitogen-activated protein kinase. In aspects, the ribonucleic acid comprising SEQ ID NO:5 (and homologs thereof) is an aptamer that is capable of binding to and inhibiting the activity of a p38 mitogen-activated protein kinase. In aspects, the ribonucleic acid comprising SEQ ID NO:5 (and homologs thereof) is an aptamer that is capable of inhibiting phosphorylation of a p38 mitogen-activated protein kinase. In aspects, the ribonucleic acid comprising SEQ ID NO:5 (and homologs thereof) is an aptamer that is capable of binding to a p38 mitogen-activated protein kinase. In aspects, the ribonucleic acid comprising SEQ ID NO:5 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: CAATCAGCGCCATCGTTGGTTGGGGTGCTTGTTTCCTGCC (SEQ ID NO:6). In SEQ ID NO:6, each U and each C is a 2F'-modified pyrimidine. In aspects, the disclosure provides a ribonucleic acid having at least 50% sequence identity to SEQ ID NO:6. In aspects, the ribonucleic acid has at least 55% sequence identity to SEQ ID NO:6. In aspects, the ribonucleic acid has at least 60% sequence identity to SEQ ID NO:6. In aspects, the ribonucleic acid has at least 65% sequence identity to SEQ ID NO:6. In aspects, the ribonucleic acid has at least 70% sequence identity to SEQ ID NO:6. In aspects, the ribonucleic acid has at least 75% sequence identity to SEQ ID NO:6. In aspects, the ribonucleic acid has at least 80% sequence identity to SEQ ID NO:6. In aspects, the ribonucleic acid has at least 85% sequence identity to SEQ ID NO:6. In aspects, the ribonucleic acid has at least 90% sequence identity to SEQ ID NO:6. In aspects, the ribonucleic acid has at least 92% sequence identity to SEQ ID NO:6. In aspects, the ribonucleic acid has at least 94% sequence identity to SEQ ID NO:6. In aspects, the ribonucleic acid has at least 95% sequence identity to SEQ ID NO:6. In aspects, the ribonucleic acid has at least 96% sequence identity to SEQ ID NO:6. In aspects, the ribonucleic acid has at least 98% sequence identity to SEQ ID NO:6. In aspects, the disclosure provides pharmaceutical compositions comprising any of the oligonucleotides described herein and a pharmaceutically acceptable excipient. In aspects, the ribonucleic acid comprising SEQ ID NO:6 (and homologs thereof) is an miRNA, mRNA, siRNA, or saRNA. In aspects, the ribonucleic acid comprising SEQ ID NO:6 (and homologs thereof) is an aptamer that is capable of binding to a p38 mitogen-activated protein kinase. In aspects, the ribonucleic acid comprising SEQ ID NO:6 (and homologs thereof) is an aptamer that is capable of inhibiting the activity of a p38 mitogen-activated protein kinase. In aspects, the ribonucleic acid comprising SEQ ID NO:6 (and homologs thereof) is an aptamer that is capable of binding to and inhibiting the activity of a p38 mitogen-activated protein kinase. In aspects, the ribonucleic acid comprising SEQ ID NO:6 (and homologs thereof) is an aptamer that is capable of inhibiting phosphorylation of a p38 mitogen-activated protein kinase. In aspects, the ribonucleic acid comprising SEQ ID NO:6 (and homologs thereof) is an aptamer that is capable of binding to a p38 mitogen-activated protein kinase. In aspects, the ribonucleic acid comprising SEQ ID NO:6 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: GGGAGACAAGAATAAACGCTCAACGGGACAAAATCAGTGAGCGTTGTCACTTATTCGG TGGGCTTCGACAGGAGGCTCACAACAGGC (SEQ ID NO:7). In SEQ ID NO:7, each U and each C is a 2F'-modified pyrimidine. In aspects, the disclosure provides a ribonucleic acid having at least 50% sequence identity to SEQ ID NO:7. In aspects, the ribonucleic acid has at least 55% sequence identity to SEQ ID NO:7. In aspects, the ribonucleic acid has at least 60% sequence identity to SEQ ID NO:7. In aspects, the ribonucleic acid has at least 65% sequence identity to SEQ ID NO:7. In aspects, the ribonucleic acid has at least 70% sequence identity to SEQ ID NO:7. In aspects, the ribonucleic acid has at least 75% sequence identity to SEQ ID NO:7. In aspects, the ribonucleic acid has at least 80% sequence identity to SEQ ID NO:7. In aspects, the ribonucleic acid has at least 85% sequence identity to SEQ ID NO:7. In aspects, the ribonucleic acid has at least 90% sequence identity to SEQ ID NO:7. In aspects, the ribonucleic acid has at least 92% sequence identity to SEQ ID NO:7. In aspects, the ribonucleic acid has at least 94% sequence identity to SEQ ID NO:7. In aspects, the ribonucleic acid has at least 95% sequence identity to SEQ ID NO:7. In aspects, the ribonucleic acid has at least 96% sequence identity to SEQ ID NO:7. In aspects, the ribonucleic acid has at least 98% sequence identity to SEQ ID NO:7. In aspects, the disclosure provides pharmaceutical compositions comprising any of the ribonucleic acids described herein and a pharmaceutically acceptable excipient.

In aspects, the ribonucleic acid comprising SEQ ID NO:7 (and homologs thereof) is an miRNA. In aspects, the ribonucleic acid comprising SEQ ID NO:7 (and homologs thereof) is an mRNA. In aspects, the ribonucleic acid comprising SEQ ID NO:7 (and homologs thereof) is an siRNA. In aspects, the ribonucleic acid comprising SEQ ID NO:7 (and homologs thereof) is an saRNA. In aspects, the ribonucleic acid comprising SEQ ID NO:7 (and homologs thereof) is an aptamer. In aspects, the ribonucleic acid comprising SEQ ID NO:7 (and homologs thereof) is an aptamer that is capable of binding to a p38 mitogen-activated protein kinase. In aspects, the ribonucleic acid comprising SEQ ID NO:7 (and homologs thereof) is an aptamer that is capable of inhibiting the activity of a p38 mitogen-activated protein kinase. In aspects, the ribonucleic acid comprising SEQ ID NO:7 (and homologs thereof) is an aptamer that is capable of binding to and inhibiting the activity of a p38 mitogen-activated protein kinase. In aspects, the ribonucleic acid comprising SEQ ID NO:7 (and homologs thereof) is an aptamer that is capable of inhibiting phosphorylation of a p38 mitogen-activated protein kinase. In aspects, the ribonucleic acid comprising SEQ ID NO:7 (and homologs thereof) is an aptamer that is capable of binding to a p38 mitogen-activated protein kinase. In aspects, the ribonucleic acid comprising SEQ ID NO:7 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

In embodiments, the disclosure provides a ribonucleic acid comprising the sequence: CGGGACAAAATCAGT-GAGCGTTGTCACTTATTCGGTGGGC (SEQ ID NO:8). In SEQ ID NO:8, each U and each C is a 2F'-modified pyrimidine. In aspects, the disclosure provides a ribonucleic acid having at least 50% sequence identity to SEQ ID NO:8. In aspects, the ribonucleic acid has at least 55% sequence identity to SEQ ID NO:8. In aspects, the ribonucleic acid has at least 60% sequence identity to SEQ ID NO:8. In aspects, the ribonucleic acid has at least 65% sequence identity to SEQ ID NO:8. In aspects, the ribonucleic acid has at least 70% sequence identity to SEQ ID NO:8. In aspects, the ribonucleic acid has at least 75% sequence identity to SEQ ID NO:8. In aspects, the ribonucleic acid has at least 80% sequence identity to SEQ ID NO:8. In aspects, the ribonucleic acid has at least 85% sequence identity to SEQ ID NO:8. In aspects, the ribonucleic acid has at least 90% sequence identity to SEQ ID NO:8. In aspects, the ribonucleic acid has at least 92% sequence identity to SEQ ID NO:8. In aspects, the ribonucleic acid has at least 94% sequence identity to SEQ ID NO:8. In aspects, the ribonucleic acid has at least 95% sequence identity to SEQ ID NO:4. In aspects, the ribonucleic acid has at least 96% sequence identity to SEQ ID NO:8. In aspects, the ribonucleic acid has at least 98% sequence identity to SEQ ID NO:8. In aspects, the disclosure provides pharmaceutical compositions comprising any of the oligonucleotides described herein and a pharmaceutically acceptable excipient. In aspects, the ribonucleic acid comprising SEQ ID NO:8 (and homologs thereof) is an miRNA, mRNA, siRNA, or saRNA. In aspects, the ribonucleic acid comprising SEQ ID NO:8 (and homologs thereof) is an aptamer that is capable of binding to a p38 mitogen-activated protein kinase. In aspects, the ribonucleic acid comprising SEQ ID NO:8 (and homologs thereof) is an aptamer that is capable of inhibiting the activity of a p38 mitogen-activated protein kinase. In aspects, the ribonucleic acid comprising SEQ ID NO:8 (and homologs thereof) is an aptamer that is capable of binding to and inhibiting the activity of a p38 mitogen-activated protein kinase. In aspects, the ribonucleic acid comprising SEQ ID NO:8 (and homologs thereof) is an aptamer that is capable of inhibiting phosphorylation of a p38 mitogen-activated protein kinase. In aspects, the ribonucleic acid comprising SEQ ID NO:8 (and homologs thereof) is an aptamer that is capable of binding to a p38 mitogen-activated protein kinase. In aspects, the ribonucleic acid comprising SEQ ID NO:8 (and homologs thereof) is an aptamer that is capable of binding to and inhibiting phosphorylation of a p38 mitogen-activated protein kinase. In aspects, the p38 mitogen-activated protein kinase is a p38γ mitogen-activated protein kinase. In aspects, the disclosure provides pharmaceutical compositions comprising any of the ribonucleic acids described herein and a pharmaceutically acceptable excipient.

The pharmaceutical compositions comprising the ribonucleic acids described herein may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10,000 mg, or 0.1 mg to about 1,000 mg, or 0.1 mg to about 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Provided herein are methods of inhibiting phosphorylation of a p38γ mitogen-activated protein kinase by contacting the p38γ mitogen-activated protein kinase with a ribonucleic acid described herein (e.g., SEQ ID NO:1, SEQ ID NO:3, or a homolog thereof). In aspects, the p38γ mitogen-activated protein kinase is located within a cell. In aspects, the p38γ mitogen-activated protein kinase is located within a mammalian cell. In aspects, the p38γ mitogen-activated protein kinase is located within a human cell. In aspects, the p38γ mitogen-activated protein kinase is located outside a cell. The contacting may be performed in vitro. The contacting may be performed in vivo. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof.

Provided herein are methods of reducing or suppressing expression of p38γ MAP kinase in a cell by contacting the cell with a ribonucleic acid described herein (e.g., SEQ ID NO:1, SEQ ID NO:3, or a homolog thereof). The contacting may be performed in vitro. The contacting may be performed in vivo. In aspects, the p38γ MAP kinase is in a mammalian cell. In aspects, the p38γ MAP kinase is in a human cell. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof.

Provided herein are methods of suppressing proliferation of a cancer cell by contacting the cancer cell with an effective amount of a p38γ kinase inhibitor described herein (e.g., SEQ ID NO:1, SEQ ID NO:3, or a homolog thereof). In aspects, the cancer cell overexpresses p38γ MAP kinase.

In aspects, the cancer cell is a breast cancer cell, a triple negative breast cancer cell, a prostate cancer cell, a colon cancer cell, an ovarian cancer cell, a lymphoma cancer cell, a cutaneous T-cell lymphoma cell, a bladder cancer cell, a lung cancer cell, a thyroid cancer cell, or a head and neck squamous carcinoma cell. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating cancer in a subject in need thereof by administering to the subject an effective amount of a p38γ kinase inhibitor described herein (e.g., SEQ ID NO:1, SEQ ID NO:3, or a homolog thereof). In aspects, the cancer overexpresses p38γ MAP kinase. In aspects, the cancer is lymphoma, cutaneous T-cell lymphoma, breast cancer, triple negative breast cancer, prostate cancer, colon cancer, ovarian cancer, bladder cancer, lung cancer, thyroid cancer, or head and neck squamous cell carcinoma. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating breast cancer in a subject in need thereof by administering to the subject an effective amount of a p38γ kinase inhibitor described herein (e.g., SEQ ID NO:1, SEQ ID NO:3, or a homolog thereof). In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the breast cancer overexpresses p38γ MAP kinase. In aspects, the breast cancer is triple negative breast cancer. In aspects, the triple negative breast cancer overexpresses p38γ MAP kinase. In aspects, the method further comprises administering an effective amount of a second anti-cancer agent.

Provided herein is a method of treating prostate cancer in a subject in need thereof by administering to the subject an effective amount of a p38γ kinase inhibitor described herein (e.g., SEQ ID NO:1, SEQ ID NO:3, or a homolog thereof). In aspects, the prostate cancer overexpresses p38γ MAP kinase. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating colon cancer in a subject in need thereof by administering to the subject an effective amount of a p38γ kinase inhibitor described herein (e.g., SEQ ID NO:1, SEQ ID NO:3, or a homolog thereof). In aspects, the colon cancer overexpresses p38γ MAP kinase. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating ovarian cancer in a subject in need thereof by administering to the subject an effective amount of a p38γ kinase inhibitor described herein (e.g., SEQ ID NO:1, SEQ ID NO:3, or a homolog thereof). In aspects, the ovarian cancer overexpresses p38γ MAP kinase. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating lymphoma in a subject in need thereof by administering to the subject an effective amount of a p38γ kinase inhibitor described herein (e.g., SEQ ID NO:1, SEQ ID NO:3, or a homolog thereof). In aspects, the lymphoma overexpresses p38γ MAP kinase. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

Provided herein is a method of treating a cutaneous T-cell lymphoma (CTCL) in a subject in need thereof by administering to the subject an effective amount of a p38γ kinase inhibitor described herein (e.g., SEQ ID NO:1, SEQ ID NO:3, or a homolog thereof). In aspects, the cutaneous T-cell lymphoma overexpresses p38γ MAP kinase. In aspects, the p38γ kinase inhibitor is a ribonucleic acid. In aspects, the ribonucleic acid comprises SEQ ID NO:1 or a homolog thereof. In aspects, the ribonucleic acid comprises SEQ ID NO:2 or a homolog thereof. In aspects, the ribonucleic acid comprises SEQ ID NO:3 or a homolog thereof. In aspects, the ribonucleic acid comprises SEQ ID NO:4 or a homolog thereof. In aspects, the ribonucleic acid comprises SEQ ID NO:5 or a homolog thereof. In aspects, the ribonucleic acid comprises SEQ ID NO:6 or a homolog thereof. In aspects, the ribonucleic acid comprises SEQ ID NO:7 or a homolog thereof. In aspects, the ribonucleic acid comprises SEQ ID NO:8 or a homolog thereof. In aspects, the method further comprises administering an effective amount of a second anti-cancer agent.

In aspects, the methods of treating cancer (e.g., breast cancer, triple negative breast cancer, prostate cancer, colon cancer, ovarian cancer, lymphoma, cutaneous T-cell lymphoma, bladder cancer, lung cancer, thyroid cancer, head and neck squamous cell carcinoma, or any cancer that overexpresses p38γ MAP kinase inhibitor described herein) or suppressing proliferation of a cancer cell further comprise administering to the subject an effective amount of a histone deacetylase (HDAC) inhibitor (HDACi). Non-limiting examples of HDACi include the compound having the following structure:

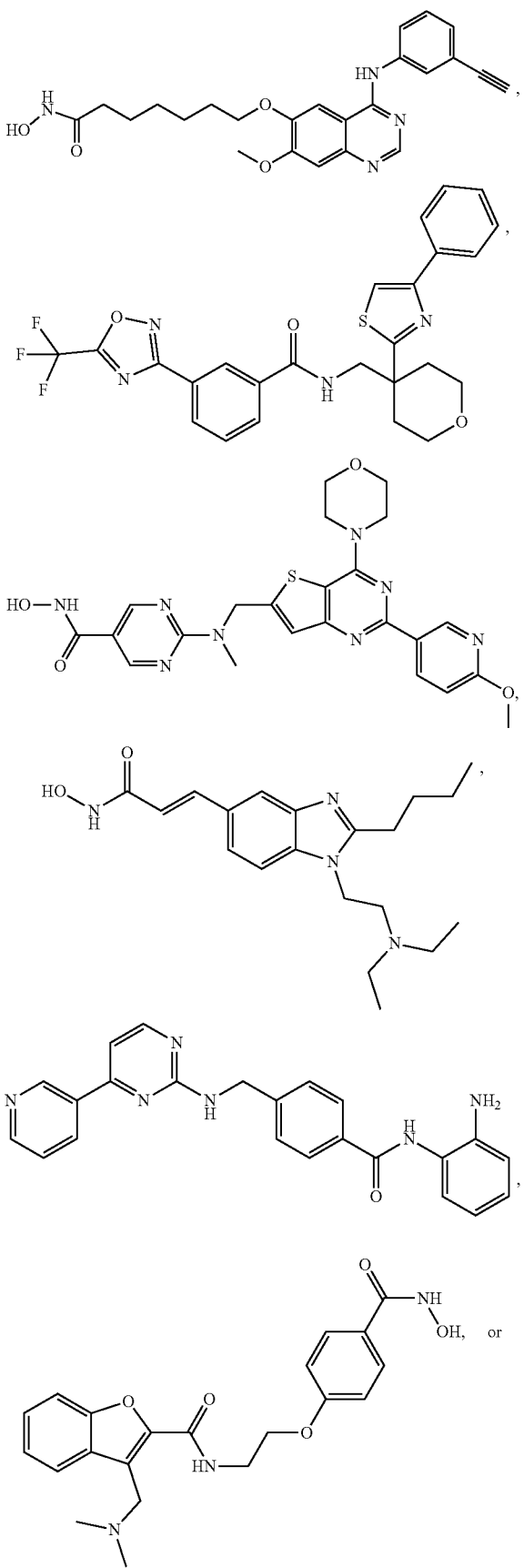

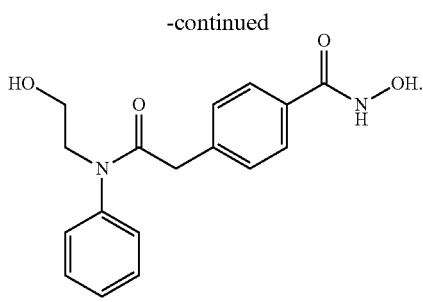

In aspects, the HDACi is vorinostat (SAHA), romidepsin, abexinostat, CI-994, belinostat, panobinostat, givinostat, entinostat, mocetinostat, trichostatin, SRT501, CUDC-101, JNJ-26481585, quisinostat, RGFP109, or PCI24781.

In aspects, the methods of treating cancer (e.g., breast cancer, triple negative breast cancer, prostate cancer, colon cancer, ovarian cancer, lymphoma, cutaneous T-cell lymphoma, bladder cancer, lung cancer, thyroid cancer, head and neck squamous cell carcinoma, or any cancer that overexpresses p38γ MAP kinase inhibitor described herein) or suppressing proliferation of a cancer cell further comprise administering to the subject an effective amount of a second anti-cancer agent. "Anti-cancer agent" is used in accordance with their plain ordinary meaning and refers to a composition (e.g. compound, drug, antagonist, inhibitor, modulator) having antineoplastic properties or the ability to inhibit the growth or proliferation of cells. In aspects, an anti-cancer agent is a chemotherapeutic. In aspects, an anti-cancer agent is an agent identified herein having utility in methods of treating cancer. In aspects, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole;

linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC- 639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

EXAMPLES

The following examples are for purposes of illustration only and are not intended to limit the spirit or scope of the claims.

Example 1

Figure 1B:
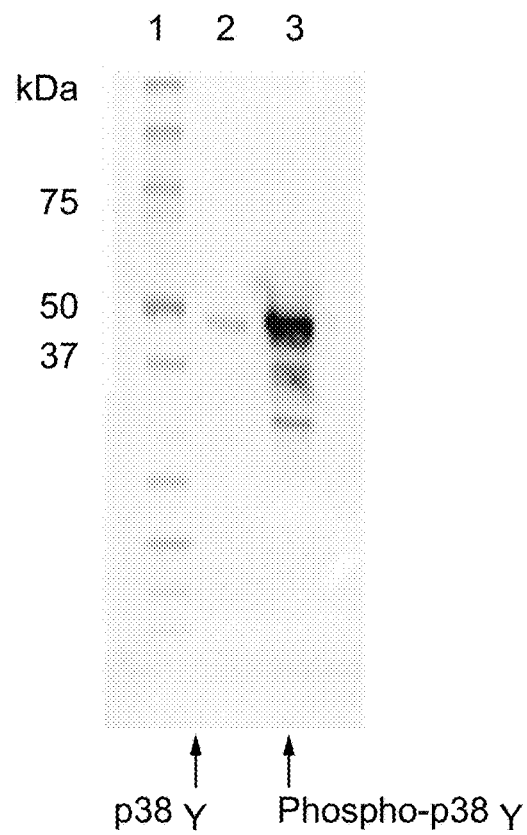
Figure 1C:
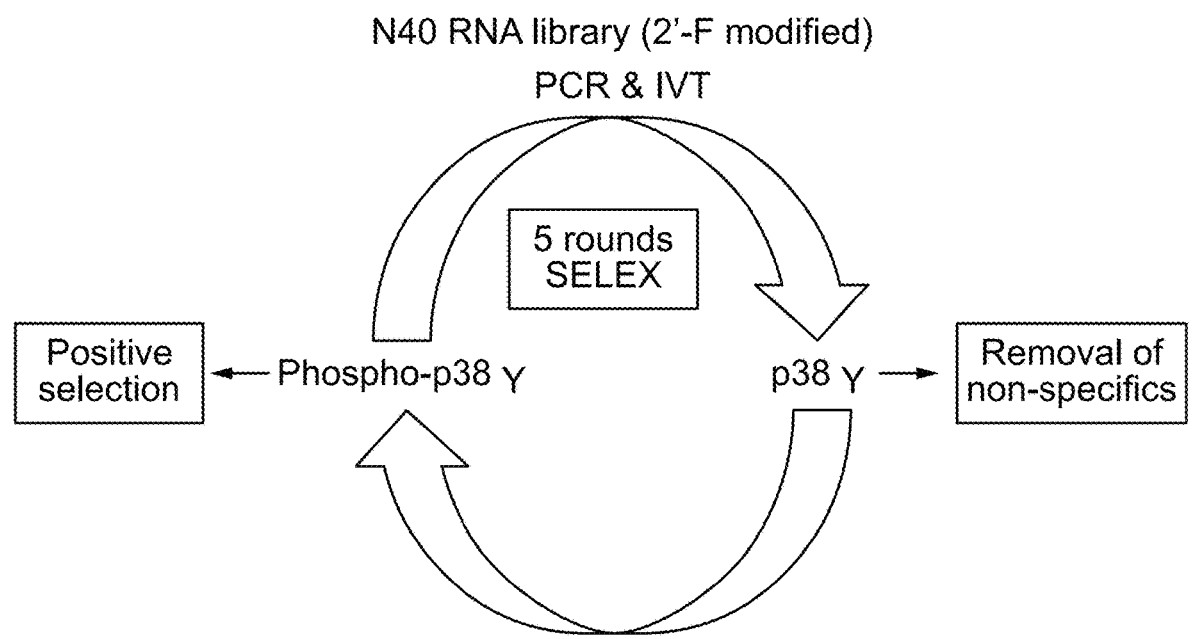
Figure 2:
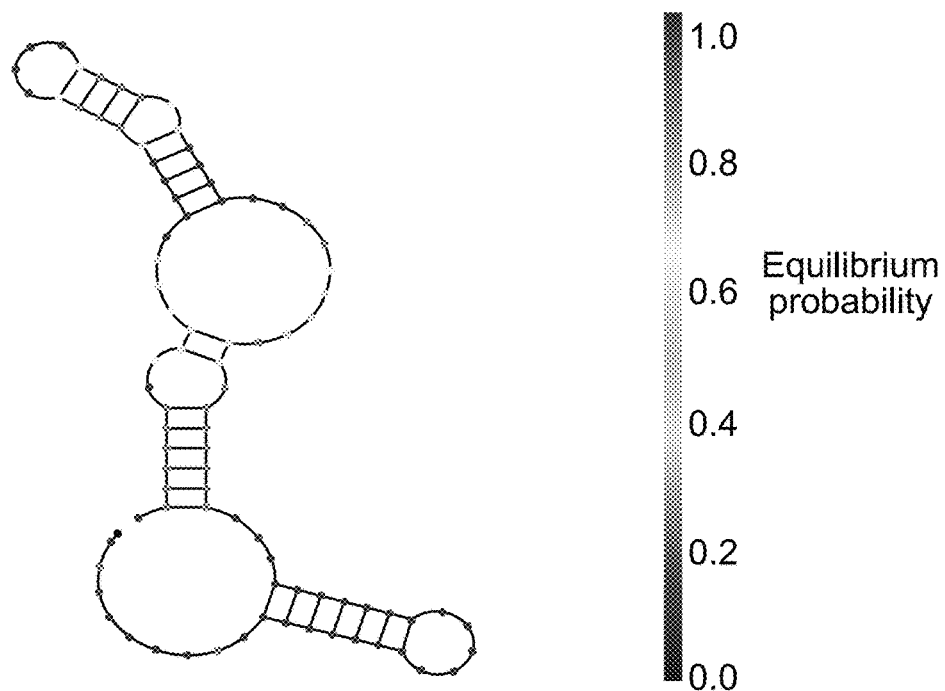
FIG. 2 shows the secondary structure of SEQ ID NO:1 at 37.0° C., which has a free energy of −23.30 kcal/mol.
Figure 3:
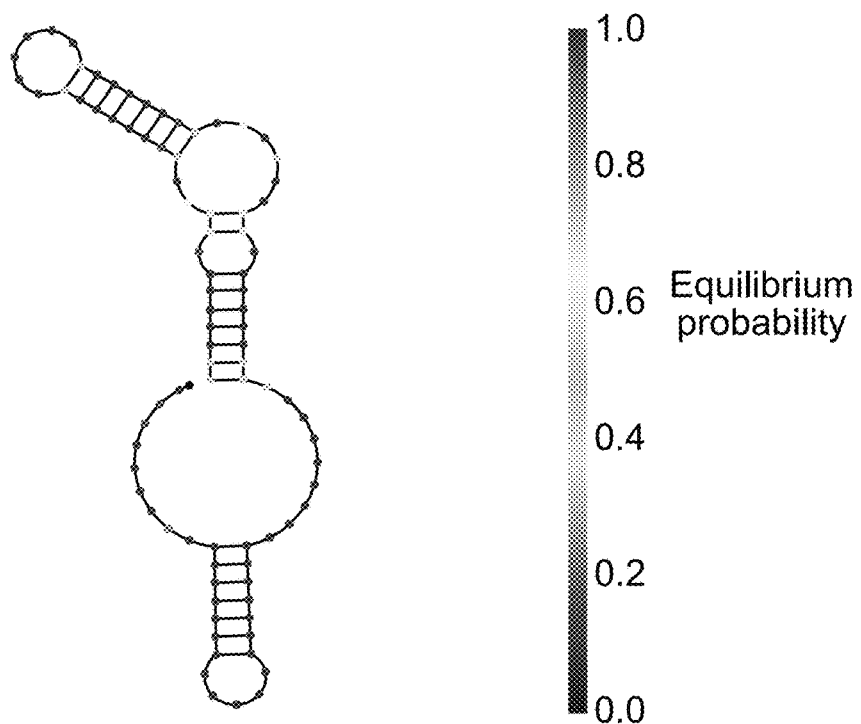
FIG. 3 shows the secondary structure of SEQ ID NO:3 at 37.0° C., which has a free energy of −28.00 kcal/mol.

Protein based systemic evaluation of ligands by exponential enrichment (SELEX) was used to select anti-p38γ RNA oligonucleotides. The target proteins used in SELEX are phosphorylated p38γ comprising Tyr-182 and Thr-185, as shown by the SDS-Page and Western Blot in FIGS. 1A and 1B, respectively. To identify oligonucleotides (e.g., ribonucleic acids or aptamers) that specifically recognize phosphorylated p38γ, non-phosphorylated p38γ was used for five rounds of the SELEX negative protein selection. The selection procedures are depicted in FIG. 1C. The sequence of each RNA aptamer clone, high throughput deep sequencing was performed through amplicon sequencing, which is a method well known in the art. After 17,996,683 reads in total in deep sequencing, the enrichment was confirmed. By combining analytical methods (enrichment, structure analysis, common motif analysis), p38γ specific aptamer of SEQ ID NO:1, SEQ ID NO:3, SEQ ID NO:5, and SEQ ID NO:7 were selected. The secondary structures SEQ ID NO:1 and SEQ ID NO:3 are depicted in FIGS. 2 and 3, respectively, as predicted by NUPACK. In SEQ ID NOS:1-8, each U and each C is a 2F'-modified pyrimidine.

Example 2

A luminescent kinase activity inhibition assay was conducted utilizing aptamers of SEQ ID NO:1 (P38-Y1), SEQ ID NO:3 (P38-Y2), SEQ ID NO:5 (P38-Y3), SEQ ID NO:7 (P38-Y7), SEQ ID NO:9 (IRRE-1), and SEQ ID NO:10 (IRRE-2). To determine inhibition of kinase activity, human recombinant p38γ proteins and ADP-Glo kits was purchased Promega. The p38 kinase was preincubated with 500 ng of the anti-p38γ RNA aptamers (e.g., P38Y-1, P38-Y2, P38-Y3, P38-Y7) for 30 mins before substrates were added, followed by addition of ATP. Then, ADP-Glo reagent was incubated in the mixture at room temperature, followed by incubation of Kinase detection reagent (Promega).

Figure 4:
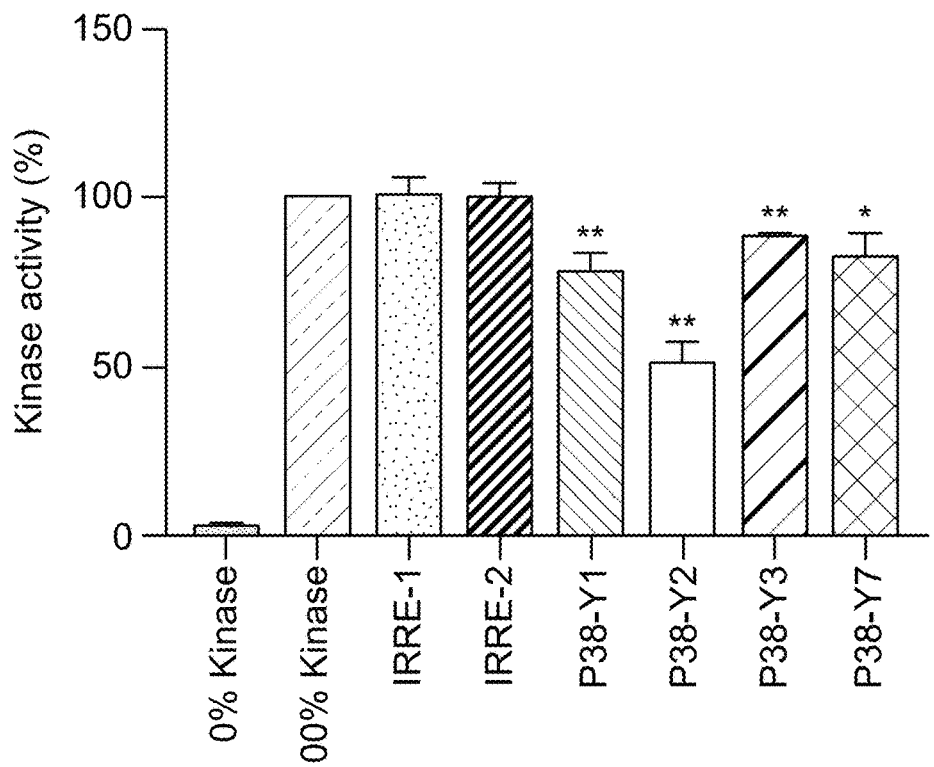
FIG. 4 shows the kinase activity inhibition of oligonucleotides including SEQ ID NO:1 (P38-Y1), SEQ ID NO:3 (P38-Y2), SEQ ID NO:5 (P38-Y3), SEQ ID NO:7 (P38-Y7) and irrelevant oligonucleotides SEQ ID NO:9 (IRRE1) and SEQ ID NO:10 (IRRE2).

With reference to FIG. 4, SEQ ID NO:1 (P38-Y1) significantly inhibited kinase activity by 50% compared to controls; SEQ ID NO:3 (P38-Y2) significantly inhibited kinase activity by 20% compared to controls; SEQ ID NO:5 (P38-Y3) significantly inhibited kinase activity by 11% compared to controls; and SEQ ID NO:7 (P38-Y3) significantly inhibited kinase activity by 18% compared to controls. The controls are SEQ ID NOS:9-10.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Informal Sequence Listing

```
(P38-γ1)
                                                           SEQ ID NO: 1
GGGAGACAAGAAUAAACGCUCAAGUGUUUUUGAAGCGUCAGCUAUAGUUGGUCUUCUUAGAGC

UUCGACAGGAGGCUCACAACAGGC

SEQ ID NO: 2
GUGUUUUUGAAGCGUCAGCUAUAGUUGGUCUUCUUAGAGC (P38-γ2)
                                                           SEQ ID NO: 3
GGGAGACAAGAAUAAACGCUCAAAACAGCGUUUGCUAUAGUUGGUCUCUCCUAAUCAACGAGC

UUCGACAGGAGGCUCACAACAGGC

SEQ ID NO: 4
AACAGCGUUUGCUAUAGUUGGUCUCUCCUAAUCAACGAGC (P38-γ3)
                                                           SEQ ID NO: 5
GGGAGACAAGAATAAACGCTCAACAATCAGCGCCATCGTTGGTTGGGGTGCTTGTTTCCTGCC

TTCGACAGGAGGCTCACAACAGGC

SEQ ID NO: 6
CAATCAGCGCCATCGTTGGTTGGGGTGCTTGTTTCCTGCC (P38-γ7)
                                                           SEQ ID NO: 7
GGGAGACAAGAATAAACGCTCAACGGGACAAAATCAGTGAGCGTTGTCACTTATTCGGTGGGC

TTCGACAGGAGGCTCACAACAGGC

SEQ ID NO: 8
CGGGACAAAATCAGTGAGCGTTGTCACTTATTCGGTGGGC (IRRE1)
                                                           SEQ ID NO: 9
GGGAGACAAGAATAAACGCTCAAGAGAGTGGTAAAGCTGTCGTTGGTCTTCCATTAGAGCCCG

TTCGACAGGAGGCTCACAACAGGC (IRRE2)
                                                           SEQ ID NO: 10
GGGAGACAAGAATAAACGCTCAAGCTTGAGGGTAGCTTTAGTTGGTCTCCGACAGAGCCTCTG

TTCGACAGGAGGCTCACAACAGGC

SEQ ID NO: 11
Met Ser Gln Glu Arg Pro Thr Phe Tyr Arg Gln Glu Leu Asn Lys Thr

Ile Trp Glu Val Pro Glu Arg Tyr Gln Asn Leu Ser Pro Val Gly Ser

Gly Ala Tyr Gly Ser Val Cys Ala Ala Phe Asp Thr Lys Thr Gly Leu

Arg Val Ala Val Lys Lys Leu Ser Arg Pro Phe Gln Ser Ile Ile His

Ala Lys Arg Thr Tyr Arg Glu Leu Arg Leu Leu Lys His Met Lys His

Glu Asn Val Ile Gly Leu Leu Asp Val Phe Thr Pro Ala Arg Ser Leu

Glu Glu Phe Asn Asp Val Tyr Leu Val Thr His Leu Met Gly Ala Asp

Leu Asn Asn Ile Val Lys Cys Gln Lys Leu Thr Asp Asp His Val Gln
```

-continued

Phe Leu Ile Tyr Gln Ile Leu Arg Gly Leu Lys Tyr Ile His Ser Ala

Asp Ile Ile His Arg Asp Leu Lys Pro Ser Asn Leu Ala Val Asn Glu

Asp Cys Glu Leu Lys Ile Leu Asp Phe Gly Leu Ala Arg His Thr Asp

Asp Glu Met Thr Gly Tyr Val Ala Thr Arg Trp Tyr Arg Ala Pro Glu

Ile Met Leu Asn Trp Met His Tyr Asn Gln Thr Val Asp Ile Trp Ser

Val Gly Cys Ile Met Ala Glu Leu Leu Thr Gly Arg Thr Leu Phe Pro

Gly Thr Asp His Ile Asp Gln Leu Lys Leu Ile Leu Arg Leu Val Gly

Thr Pro Gly Ala Glu Leu Leu Lys Lys Ile Ser Ser Glu Ser Ala Arg

Asn Tyr Ile Gln Ser Leu Thr Gln Met Pro Lys Met Asn Phe Ala Asn

Val Phe Ile Gly Ala Asn Pro Leu Ala Val Asp Leu Leu Glu Lys Met

Leu Val Leu Asp Ser Asp Lys Arg Ile Thr Ala Ala Gln Ala Leu Ala

His Ala Tyr Phe Ala Gln Tyr His Asp Pro Asp Asp Glu Pro Val Ala

Asp Pro Tyr Asp Gln Ser Phe Glu Ser Arg Asp Leu Leu Ile Asp Glu

Trp Lys Ser Leu Thr Tyr Asp Glu Val Ile Ser Phe Val Pro Pro Pro

Leu Asp Gln Glu Glu Met Glu Ser

SEQ ID NO: 12
Met Ser Gly Pro Arg Ala Gly Phe Tyr Arg Gln Glu Leu Asn Lys Thr

Val Trp Glu Val Pro Gln Arg Leu Gln Gly Leu Arg Pro Val Gly Ser

Gly Ala Tyr Gly Ser Val Cys Ser Ala Tyr Asp Ala Arg Leu Arg Gln

Lys Val Ala Val Lys Lys Leu Ser Arg Pro Phe Gln Ser Leu Ile His

Ala Arg Arg Thr Tyr Arg Glu Leu Arg Leu Leu Lys His Leu Lys His

Glu Asn Val Ile Gly Leu Leu Asp Val Phe Thr Pro Ala Thr Ser Ile

Glu Asp Phe Ser Glu Val Tyr Leu Val Thr Thr Leu Met Gly Ala Asp

Leu Asn Asn Ile Val Lys Cys Gln Ala Leu Ser Asp Glu His Val Gln

Phe Leu Val Tyr Gln Leu Leu Arg Gly Leu Lys Tyr Ile His Ser Ala

Gly Ile Ile His Arg Asp Leu Lys Pro Ser Asn Val Ala Val Asn Glu

Asp Cys Glu Leu Arg Ile Leu Asp Phe Gly Leu Ala Arg Gln Ala Asp

Glu Glu Met Thr Gly Tyr Val Ala Thr Arg Trp Tyr Arg Ala Pro Glu

Ile Met Leu Asn Trp Met His Tyr Asn Gln Thr Val Asp Ile Trp Ser

Val Gly Cys Ile Met Ala Glu Leu Leu Gln Gly Lys Ala Leu Phe Pro

Gly Ser Asp Tyr Ile Asp Gln Leu Lys Arg Ile Met Glu Val Val Gly

Thr Pro Ser Pro Glu Val Leu Ala Lys Ile Ser Ser Glu His Ala Arg

Thr Tyr Ile Gln Ser Leu Pro Pro Met Pro Gln Lys Asp Leu Ser Ser

Ile Phe Arg Gly Ala Asn Pro Leu Ala Ile Asp Leu Leu Gly Arg Met

Leu Val Leu Asp Ser Asp Gln Arg Val Ser Ala Ala Glu Ala Leu Ala

His Ala Tyr Phe Ser Gln Tyr His Asp Pro Glu Asp Glu Pro Glu Ala

Glu Pro Tyr Asp Glu Ser Val Glu Ala Lys Glu Arg Thr Leu Glu Glu

Trp Lys Glu Leu Thr Tyr Gln Glu Val Leu Ser Phe Lys Pro Pro Glu

Pro Pro Lys Pro Pro Gly Ser Leu Glu Ile Glu Gln

SEQ ID NO: 13
Met Ser Ser Pro Pro Ala Arg Ser Gly Phe Tyr Arg Gln Glu Val

Thr Lys Thr Ala Trp Glu Val Arg Ala Val Tyr Arg Asp Leu Gln Pro

-continued

```
Val Gly Ser Gly Ala Tyr Gly Ala Val Cys Ser Ala Val Asp Gly Arg
Thr Gly Ala Lys Val Ala Ile Lys Lys Leu Tyr Arg Pro Phe Gln Ser
Glu Leu Phe Ala Lys Arg Ala Tyr Arg Glu Leu Arg Leu Leu Lys His
Met Arg His Glu Asn Val Ile Gly Leu Leu Asp Val Phe Thr Pro Asp
Glu Thr Leu Asp Asp Phe Thr Asp Phe Tyr Leu Val Met Pro Phe Met
Gly Thr Asp Leu Gly Lys Leu Met Lys His Glu Lys Leu Gly Glu Asp
Arg Ile Gln Phe Leu Val Tyr Gln Met Leu Lys Gly Leu Arg Tyr Ile
His Ala Ala Gly Ile Ile His Arg Asp Leu Lys Pro Gly Asn Leu Ala
Val Asn Glu Asp Cys Glu Leu Lys Ile Leu Asp Phe Gly Leu Ala Arg
Gln Ala Asp Ser Glu Met Thr Gly Tyr Val Val Thr Arg Trp Tyr Arg
Ala Pro Glu Val Ile Leu Asn Trp Met Arg Tyr Thr Gln Thr Val Asp
Ile Trp Ser Val Gly Cys Ile Met Ala Glu Met Ile Thr Gly Lys Thr
Leu Phe Lys Gly Ser Asp His Leu Asp Gln Leu Lys Glu Ile Met Lys
Val Thr Gly Thr Pro Pro Ala Glu Phe Val Gln Arg Leu Gln Ser Asp
Glu Ala Lys Asn Tyr Met Lys Gly Leu Pro Glu Leu Glu Lys Lys Asp
Phe Ala Ser Ile Leu Thr Asn Ala Ser Pro Leu Ala Val Asn Leu Leu
Glu Lys Met Leu Val Leu Asp Ala Glu Gln Arg Val Thr Ala Gly Glu
Ala Leu Ala His Pro Tyr Phe Glu Ser Leu His Asp Thr Glu Asp Glu
Pro Gln Val Gln Lys Tyr Asp Asp Ser Phe Asp Asp Val Asp Arg Thr
Leu Asp Glu Trp Lys Arg Val Thr Tyr Lys Glu Val Leu Ser Phe Lys
Pro Pro Arg Gln Leu Gly Ala Arg Val Ser Lys Glu Thr Pro Leu

SEQ ID NO: 14
Met Ser Leu Ile Arg Lys Lys Gly Phe Tyr Lys Gln Asp Val Asn Lys
Thr Ala Trp Glu Leu Pro Lys Thr Tyr Val Ser Pro Thr His Val Gly
Ser Gly Ala Tyr Gly Ser Val Cys Ser Ala Ile Asp Lys Arg Ser Gly
Glu Lys Val Ala Ile Lys Lys Leu Ser Arg Pro Phe Gln Ser Glu Ile
Phe Ala Lys Arg Ala Tyr Arg Glu Leu Leu Leu Leu Lys His Met Gln
His Glu Asn Val Ile Gly Leu Leu Asp Val Phe Thr Pro Ala Ser Ser
Leu Arg Asn Phe Tyr Asp Phe Tyr Leu Val Met Pro Phe Met Gln Thr
Asp Leu Gln Lys Ile Met Gly Met Glu Phe Ser Glu Glu Lys Ile Gln
Tyr Leu Val Tyr Gln Met Leu Lys Gly Leu Lys Tyr Ile His Ser Ala
Gly Val Val His Arg Asp Leu Lys Pro Gly Asn Leu Ala Val Asn Glu
Asp Cys Glu Leu Lys Ile Leu Asp Phe Gly Leu Ala Arg His Ala Asp
Ala Glu Met Thr Gly Tyr Val Val Thr Arg Trp Tyr Arg Ala Pro Glu
Val Ile Leu Ser Trp Met His Tyr Asn Gln Thr Val Asp Ile Trp Ser
Val Gly Cys Ile Met Ala Glu Met Leu Thr Gly Lys Thr Leu Phe Lys
Gly Lys Asp Tyr Leu Asp Gln Leu Thr Gln Ile Leu Lys Val Thr Gly
Val Pro Gly Thr Glu Phe Val Gln Lys Leu Asn Asp Lys Ala Ala Lys
Ser Tyr Ile Gln Ser Leu Pro Gln Thr Pro Arg Lys Asp Phe Thr Gln
Leu Phe Pro Arg Ala Ser Pro Gln Ala Ala Asp Leu Leu Glu Lys Met
Leu Glu Leu Asp Val Asp Lys Arg Leu Thr Ala Ala Gln Ala Leu Thr
```

-continued

His Pro Phe Phe Glu Pro Phe Arg Asp Pro Glu Glu Glu Thr Glu Ala

Gln Gln Pro Phe Asp Asp Ser Leu Glu His Glu Lys Leu Thr Val Asp

Glu Trp Lys Gln His Ile Tyr Lys Glu Ile Val Asn Phe Ser Pro Ile

Ala Arg Lys Asp Ser Arg Arg Arg Ser Gly Met Lys Leu

What is claimed is:

1. A ribonucleic acid comprising SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

2. The ribonucleic acid of claim 1, comprising SEQ ID NO:2.

3. The ribonucleic acid of claim 1, comprising SEQ ID NO:3.

4. The ribonucleic acid of claim 1, comprising SEQ ID NO:4.

5. The ribonucleic acid of claim 1, comprising SEQ ID NO:5.

6. The ribonucleic acid of claim 1, wherein the ribonucleic acid is an aptamer that inhibits phosphorylation of a p38γ mitogen-activated protein kinase.

7. A pharmaceutical composition comprising the ribonucleic acid of claim 1 and a pharmaceutically acceptable carrier.

8. A method of treating cancer in a patient in need thereof, the method comprising administering to the patient a therapeutically effective amount of the ribonucleic acid of claim 1.

9. The method of claim 8, wherein the cancer is breast cancer, prostate cancer, colon cancer, ovarian cancer, bladder cancer, lung cancer, thyroid cancer, or a head and neck squamous cell carcinoma.

10. The method of claim 8, wherein the cancer is lymphoma.

11. The method of claim 8, wherein the cancer is cutaneous T-cell lymphoma.

12. The method of claim 8, wherein the cancer overexpresses p38γ mitogen-activated protein kinase.

13. A method of suppressing proliferation of a cutaneous T-cell lymphoma cell, the method comprising contacting the cutaneous T-cell lymphoma cell with an effective amount of the ribonucleic acid of claim 1; thereby suppressing proliferation of the cutaneous T-cell lymphoma cell.

14. A method of suppressing proliferation of a cancer cell that overexpresses p38γ mitogen-activated protein kinase, the method comprising contacting the cancer cell with an effective amount of the ribonucleic acid of claim 1; thereby suppressing proliferation of the cancer cell.

15. A method of inhibiting phosphorylation of a p38γ mitogen-activated protein kinase, the method comprising contacting the p38γ mitogen-activated protein kinase with an effective amount of the ribonucleic acid of claim 1; thereby inhibiting phosphorylation of p38γ mitogen-activated protein kinase.

16. The ribonucleic acid of claim 1, comprising SEQ ID NO:6.

17. The ribonucleic acid of claim 1, comprising SEQ ID NO:7.

18. The ribonucleic acid of claim 1, comprising SEQ ID NO:8.

19. The ribonucleic acid of claim 5, comprising SEQ ID NO:1.

20. The ribonucleic acid of claim 1, having the sequence as set forth in SEQ ID NO:1.

* * * * *

SEQUENCE LISTING

<160> NUMBER OF SEQ ID NOS: 14

<210> SEQ ID NO 1
<211> LENGTH: 87
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P38-gamma1

<400> SEQUENCE: 1
gggagacaag aauaaacgcu caaguguuuu ugaagcguca gcuauaguug gucuucuuag      60
agcuucgaca ggaggcucac aacaggc                                         87

<210> SEQ ID NO 2
<211> LENGTH: 40
<212> TYPE: RNA
<213> ORGANISM: Artificial sequence
<220> FEATURE:
<223> OTHER INFORMATION: Synthetic polynucleotide

<400> SEQUENCE: 2
guguuuuuga agcgucagcu auaguggguc uucuuagagc                            40

<210> SEQ ID NO 3
<211> LENGTH: 87
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P38-gamma2

<400> SEQUENCE: 3
gggagacaag aauaaacgcu caaaacagcg uuugcuauag uuggucucuc cuaaucaacg      60
agcuucgaca ggaggcucac aacaggc                                         87

<210> SEQ ID NO 4
<211> LENGTH: 40
<212> TYPE: RNA
<213> ORGANISM: Artificial sequence
<220> FEATURE:
<223> OTHER INFORMATION: Synthetic polynucleotide

<400> SEQUENCE: 4
aacagcguuu gcuauaguug gucucuccua aucaacgagc                            40

<210> SEQ ID NO 5
<211> LENGTH: 87
<212> TYPE: DNA
<213> ORGANISM: Artificial sequence
<220> FEATURE:
<223> OTHER INFORMATION: Synthetic polynucleotide

```
<220> FEATURE:
<221> NAME/KEY: misc_feature
<223> OTHER INFORMATION: P38-gamma3

<400> SEQUENCE: 5
gggagacaag aataaacgct caacaatcag cgccatcgtt ggttggggtg cttgtttcct    60
gccttcgaca ggaggctcac aacaggc                                       87

<210> SEQ ID NO 6
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 6
caatcagcgc catcgttggt tggggtgctt gtttcctgcc                          40

<210> SEQ ID NO 7
<211> LENGTH: 87
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P38-gamma7

<400> SEQUENCE: 7
gggagacaag aataaacgct caacgggaca aaatcagtga gcgttgtcac ttattcggtg    60
ggcttcgaca ggaggctcac aacaggc                                       87

<210> SEQ ID NO 8
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 8
cgggacaaaa tcagtgagcg ttgtcactta ttcggtgggc                          40

<210> SEQ ID NO 9
<211> LENGTH: 87
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: IRRE1

<400> SEQUENCE: 9
gggagacaag aataaacgct caagagagtg gtaaagctgt cgttggtctt ccattagagc    60
ccgttcgaca ggaggctcac aacaggc                                       87

<210> SEQ ID NO 10
<211> LENGTH: 87
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: IRRE2
```

<400> SEQUENCE: 10

```
gggagacaag aataaacgct caagcttgag ggtagcttta gttggtctcc gacagagcct    60
ctgttcgaca ggaggctcac aacaggc                                       87
```

<210> SEQ ID NO 11
<211> LENGTH: 360
<212> TYPE: PRT
<213> ORGANISM: Artificial sequence
<220> FEATURE:
<223> OTHER INFORMATION: Synthetic polypeptide

<400> SEQUENCE: 11

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335
```

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 12
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 12

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
        115                 120                 125

Phe Leu Val Tyr Gln Leu Leu Arg Gly Leu Lys Tyr Ile His Ser Ala
    130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Gln Gly Lys Ala Leu Phe Pro
210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
            260                 265                 270

Ile Phe Arg Gly Ala Asn Pro Leu Ala Ile Asp Leu Leu Gly Arg Met
        275                 280                 285

Leu Val Leu Asp Ser Asp Gln Arg Val Ser Ala Ala Glu Ala Leu Ala
    290                 295                 300

His Ala Tyr Phe Ser Gln Tyr His Asp Pro Glu Asp Glu Pro Glu Ala
305                 310                 315                 320

Glu Pro Tyr Asp Glu Ser Val Glu Ala Lys Glu Arg Thr Leu Glu Glu
                325                 330                 335

Trp Lys Glu Leu Thr Tyr Gln Glu Val Leu Ser Phe Lys Pro Pro Glu
                340                 345                 350

Pro Pro Lys Pro Pro Gly Ser Leu Glu Ile Glu Gln
        355                 360

<210> SEQ ID NO 13
<211> LENGTH: 367
<212> TYPE: PRT
<213> ORGANISM: Artificial sequence
<220> FEATURE:
<223> OTHER INFORMATION: Synthetic polypeptide

<400> SEQUENCE: 13

Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
                20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
    50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
        195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
        275                 280                 285

Glu Lys Met Leu Val Leu Asp Ala Glu Gln Arg Val Thr Ala Gly Glu
        290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

```
Leu Asp Glu Trp Lys Arg Val Thr Tyr Lys Glu Val Leu Ser Phe Lys
                340                 345                 350

Pro Pro Arg Gln Leu Gly Ala Arg Val Ser Lys Glu Thr Pro Leu
            355                 360                 365
```

<210> SEQ ID NO 14
<211> LENGTH: 365
<212> TYPE: PRT
<213> ORGANISM: Artificial sequence
<220> FEATURE:
<223> OTHER INFORMATION: Synthetic polypeptide

<400> SEQUENCE: 14

```
Met Ser Leu Ile Arg Lys Lys Gly Phe Tyr Lys Gln Asp Val Asn Lys
 1               5                  10                  15

Thr Ala Trp Glu Leu Pro Lys Thr Tyr Val Ser Pro Thr His Val Gly
                20                  25                  30

Ser Gly Ala Tyr Gly Ser Val Cys Ser Ala Ile Asp Lys Arg Ser Gly
            35                  40                  45

Glu Lys Val Ala Ile Lys Lys Leu Ser Arg Pro Phe Gln Ser Glu Ile
        50                  55                  60

Phe Ala Lys Arg Ala Tyr Arg Glu Leu Leu Leu Lys His Met Gln
 65                 70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Lys Ile Gln
        115                 120                 125

Tyr Leu Val Tyr Gln Met Leu Lys Gly Leu Lys Tyr Ile His Ser Ala
130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
290                 295                 300

His Pro Phe Phe Glu Pro Phe Arg Asp Pro Glu Glu Thr Glu Ala
305                 310                 315                 320

Gln Gln Pro Phe Asp Asp Ser Leu Glu His Glu Lys Leu Thr Val Asp
                325                 330                 335
```

```
-continued

Glu Trp Lys Gln His Ile Tyr Lys Glu Ile Val Asn Phe Ser Pro Ile
            340                 345                 350

Ala Arg Lys Asp Ser Arg Arg Arg Ser Gly Met Lys Leu
        355             360                 365
```

UNITED STATES PATENT AND TRADEMARK OFFICE
CERTIFICATE OF CORRECTION

Page 1 of 1

PATENT NO. : 11,225,665 B2
APPLICATION NO. : 16/902029
DATED : January 18, 2022
INVENTOR(S) : John J. Rossi and Sorah Yoon It is certified that error appears in the above-identified patent and that said Letters Patent is hereby corrected as shown below:

In the Specification

At Column 1, Line 15, delete "grant no. NIHAII29329 awarded by the National Institute of" and insert the following -- AI129329 awarded by the National Institutes of --

Signed and Sealed this
Second Day of September, 2025

Coke Morgan Stewart
*Acting Director of the United States Patent and Trademark Office*